United States Patent
Li et al.

(10) Patent No.: US 10,576,099 B2
(45) Date of Patent: Mar. 3, 2020

(54) INJECTABLE SCAFFOLD FOR TREATMENT OF INTRACRANIAL ANEURYSMS AND RELATED TECHNOLOGY

(71) Applicant: Covidien LP, Mansfield, MA (US)

(72) Inventors: Junwei Li, Irvine, CA (US); Gaurav Girdhar, Ladera Ranch, CA (US); John Wainwright, Foothill Ranch, CA (US); Yves Bayon, Lyons (FR); Ariana Pagnani, Long Beach, CA (US)

(73) Assignee: Covidien LP, Mansfield, MA (US)

( * ) Notice: Subject to any disclaimer, the term of this patent is extended or adjusted under 35 U.S.C. 154(b) by 520 days.

(21) Appl. No.: 15/299,929

(22) Filed: Oct. 21, 2016

(65) Prior Publication Data
US 2018/0110797 A1   Apr. 26, 2018

(51) Int. Cl.
*A61K 31/722* (2006.01)
*A61M 5/145* (2006.01)
(Continued)

(52) U.S. Cl.
CPC ...... *A61K 31/722* (2013.01); *A61B 17/12186* (2013.01); *A61M 5/1452* (2013.01); *A61M 25/10* (2013.01); *A61M 2210/0687* (2013.01)

(58) Field of Classification Search
CPC ........ A61B 17/12031; A61B 17/12113; A61B 17/12195; A61B 17/12186; A61B 17/12181; A61L 2430/36; A61K 31/722
See application file for complete search history.

(56) References Cited

U.S. PATENT DOCUMENTS 5,354,295 A   10/1994 Guglielmi et al.
5,669,931 A   9/1997 Kupiecki et al.
(Continued)

FOREIGN PATENT DOCUMENTS

| WO | 2011066962 A1 | 6/2011 |
| WO | 2017074411 A1 | 5/2017 |
| WO | 2018051187 A1 | 3/2018 |

OTHER PUBLICATIONS

Barnett et al., Assessment of EmboGel—A Selectively Dissolvable Radiopaque Hydrogel for Embolic Applications, Journal of Vascular and Interventional Radiology: JVIR, Feb. 2011, 10 pages.
(Continued)

*Primary Examiner* — Ashley L Fishback
(74) *Attorney, Agent, or Firm* — Fortem IP LLP; Vijay Kumar

(57) ABSTRACT

A method for treating an aneurysm in accordance with a particular embodiment of the present technology includes intravascularly delivering a mixture including a biopolymer (e.g., chitosan) and a chemical crosslinking agent (e.g., genipin) to an aneurysm. The method further includes mixing the biopolymer and the chemical crosslinking agent to initiate chemical crosslinking of the biopolymer. The mixture is delivered to the aneurysm via a lumen and an exit port of a catheter while the chemical crosslinking is ongoing. The mixture exits the catheter as a single cohesive strand that at least partially agglomerates to form a mass occupying at least 75% of a total internal volume of the aneurysm. During delivery of the mixture, the method includes expanding a tubular flow diverter to reinforce a neck of the aneurysm.

20 Claims, 9 Drawing Sheets

(51) Int. Cl.
*A61M 25/10* (2013.01)
*A61B 17/12* (2006.01)

(56) References Cited

U.S. PATENT DOCUMENTS

| | | | |
|---|---|---|---|
| 5,951,599 | A | 9/1999 | McCrory |
| 6,309,367 | B1 | 10/2001 | Boock |
| 6,591,472 | B1 * | 7/2003 | Noone .............. A61M 25/0009 264/171.13 |
| 6,602,261 | B2 | 8/2003 | Greene et al. |
| 6,605,101 | B1 | 8/2003 | Schaefer et al. |
| 6,878,384 | B2 | 4/2005 | Cruise et al. |
| 7,229,461 | B2 | 6/2007 | Chin et al. |
| 7,601,160 | B2 | 10/2009 | Richter |
| RE42,625 | E | 8/2011 | Guglielmi |
| 8,043,326 | B2 | 10/2011 | Hancock et al. |
| 8,425,541 | B2 | 4/2013 | Masters et al. |
| 8,470,013 | B2 | 6/2013 | Duggal et al. |
| 8,715,317 | B1 | 5/2014 | Janardhan et al. |
| 8,906,057 | B2 | 12/2014 | Connor et al. |
| 9,211,202 | B2 | 12/2015 | Strother et al. |
| 9,486,224 | B2 | 11/2016 | Riina et al. |
| 9,833,309 | B2 | 12/2017 | Levi et al. |
| 9,844,380 | B2 | 12/2017 | Furey |
| 9,907,684 | B2 | 3/2018 | Connor et al. |
| 9,962,146 | B2 | 5/2018 | Hebert et al. |
| 10,028,745 | B2 | 7/2018 | Morsi |
| 2001/0000797 | A1 | 5/2001 | Mazzocchi |
| 2001/0001835 | A1 | 5/2001 | Greene et al. |
| 2003/0018294 | A1 | 1/2003 | Cox |
| 2003/0028209 | A1 | 2/2003 | Teoh et al. |
| 2003/0040772 | A1 | 2/2003 | Hyodoh et al. |
| 2005/0267511 | A1 | 12/2005 | Marks et al. |
| 2006/0155323 | A1 | 7/2006 | Porter et al. |
| 2006/0200234 | A1 | 9/2006 | Hines |
| 2006/0206199 | A1 | 9/2006 | Churchwell et al. |
| 2007/0014831 | A1 * | 1/2007 | Sung ................ A61B 17/12022 424/426 |
| 2007/0100426 | A1 | 5/2007 | Rudakov et al. |
| 2007/0175536 | A1 | 8/2007 | Monetti et al. |
| 2007/0191924 | A1 | 8/2007 | Rudakov |
| 2010/0144895 | A1 | 6/2010 | Porter |
| 2011/0137405 | A1 | 6/2011 | Wilson et al. |
| 2012/0316632 | A1 | 12/2012 | Gao |
| 2013/0274866 | A1 | 10/2013 | Cox et al. |
| 2014/0012307 | A1 | 1/2014 | Franano et al. |
| 2014/0058420 | A1 | 2/2014 | Hannes et al. |
| 2014/0316012 | A1 | 10/2014 | Freyman et al. |
| 2014/0371734 | A1 | 12/2014 | Truckai |
| 2015/0216684 | A1 | 8/2015 | Enzmann et al. |
| 2015/0250628 | A1 | 9/2015 | Monstadt et al. |
| 2015/0313737 | A1 | 11/2015 | Tippett et al. |
| 2015/0327843 | A1 | 11/2015 | Garrison |
| 2016/0066921 | A1 | 3/2016 | Seifert et al. |
| 2016/0135984 | A1 | 5/2016 | Rudakov et al. |
| 2016/0206320 | A1 | 7/2016 | Connor |
| 2016/0206321 | A1 | 7/2016 | Connor |
| 2017/0150971 | A1 | 6/2017 | Hines |
| 2017/0156903 | A1 | 6/2017 | Shobayashi |
| 2017/0189035 | A1 | 7/2017 | Porter |
| 2017/0266023 | A1 | 9/2017 | Thomas |
| 2017/0340333 | A1 | 11/2017 | Badruddin et al. |
| 2017/0367708 | A1 | 12/2017 | Mayer et al. |
| 2018/0049859 | A1 | 2/2018 | Stoppenhagen et al. |
| 2018/0125686 | A1 | 5/2018 | Lu |
| 2018/0140305 | A1 | 5/2018 | Connor |
| 2018/0161185 | A1 | 6/2018 | Kresslein et al. |
| 2018/0193025 | A1 | 7/2018 | Walzman |
| 2018/0193026 | A1 | 7/2018 | Yang et al. |
| 2018/0206852 | A1 | 7/2018 | Moeller |
| 2019/0053811 | A1 | 2/2019 | Garza et al. |

OTHER PUBLICATIONS

Berenstein et al., Treatment of Experimental Aneurysms With an Embolic-Containing Device and Liquid Embolic Agent: Feasibility and Angiographic and Histological Results, Neurosurgery, vol. 64, No. 2, Feb. 2009, 367-373.

Brennecka et al., In vivo embolization of lateral wall aneurysms in canines using the liquid-to-solid gelling PPODA-QT polymer system: 6-month pilot study, J Neurosurg, Apr. 5, 2013, pp. 1-11.

Brennecka et al., In Vivo Experimental Aneurysm Embolization in a Swine Model with a Liquid-to-Solid Gelling Polymer System: Initial Biocompatibility and Delivery Strategy Analysis, World Neurosurgery 78[5]: 469-480, Nov. 2012.

Jalani et al., Tough, in-situ thermogelling, injectable hydrogels for biomedical applications, Macromol Biosci. Apr. 2015;15(4):473-80, [Abstract only].

Murayama, et al., Endovascular Treatment of Experimental Aneurysms by Use of a Combination of Liquid Embolic Agents and Protective Devices, AJNR Am J Neuroradiol 21:1726-1735, Oct. 2000.

Ning et al., Experimental study of temperature-sensitive chitosan/ β-glycerophosphate embolic material in embolizing the basicranial rete mirabile in swines, Experimental and Therapeutic Medicine 10: 316-322, 2015.

Nonn et al., Feasibility, Safety, and Efficacy of Flow-Diverting Stent-Assisted Microsphere Embolization of Fusiform and Sidewall Aneurysms, www.neurosurgery-online.com, vol. 77, No. 1, Jul. 2015, 11 pages.

Wang et al., In Vivo Assessment of Chitosan/β-Glycerophosphate as a New Liquid Embolic Agent, Interventional Neuroradiology 17: 87-92, 2011.

Zhen et al, Embolization of aneurysm by chitosan-glycerophosphate-fibroblast tissue hydrogel, a tissue engineering material: experiment with rabbits, Nail Med J China, Mar. 24, 2009. Vo. 89, No. 11, [Abstract only].

Molyneux, et al., International Subarachnoid Aneurysm Trial (ISAT) of neurosurgical clipping versus endovascular coiling in 2143 patients with ruptured intracranial aneurysms: a randomised trial, Lancet 2002; 360: 1267-74.

Murayama, et al., Guglielmi Detachable Coil embolization of cerebral aneurysms: 11 years' experience, J Neurosurg 98:959-966, 2003.

* cited by examiner

INJECTABLE SCAFFOLD FOR TREATMENT OF INTRACRANIAL ANEURYSMS AND RELATED TECHNOLOGY

TECHNICAL FIELD

The present technology is related to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated. One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., Clause 1, Clause 13, or Clause 22.

1. A method for treating an aneurysm, the method comprising:
   intravascularly advancing a catheter toward an aneurysm at a portion of a blood vessel, wherein the catheter includes an elongate lumen and an exit port at a distal end portion of the lumen;
   mixing a biopolymer and a chemical crosslinking agent to initiate chemical crosslinking of the biopolymer;
   flowing the biopolymer and the chemical crosslinking agent toward an internal volume of the aneurysm via the lumen while the chemical crosslinking is ongoing; and delivering the biopolymer and the chemical crosslinking agent from the lumen into the internal volume via the exit port while the chemical crosslinking is ongoing.

2. The method of Clause 1 wherein the aneurysm is an intracranial aneurysm.

3. The method of Clause 1 wherein:
   the biopolymer has a non-zero degree of chemical crosslinking before being mixed with the chemical crosslinking agent; and
   mixing the biopolymer and the chemical crosslinking agent includes mixing the biopolymer and the chemical crosslinking agent to increase the degree of chemical crosslinking.

4. The method of Clause 1 wherein delivering the biopolymer and the chemical crosslinking agent from the lumen into the internal volume includes delivering the biopolymer and the chemical crosslinking agent from the lumen into the internal volume as components of a single cohesive strand that at least partially agglomerates to form a mass occupying at least 75% of the internal volume, and wherein the internal volume is a total internal volume of the aneurysm.

5. The method of Clause 1, further comprising:
   flowing a physical crosslinking agent toward the internal volume via the lumen with the biopolymer and the chemical crosslinking agent; and
   delivering the physical crosslinking agent from the lumen into the internal volume via the exit port with the biopolymer and the chemical crosslinking agent.

6. The method of Clause 5 wherein:
   the biopolymer includes chitosan, a derivative of chitosan, an analog of chitosan, or a combination thereof;
   the chemical crosslinking agent includes genipin, a derivative of genipin, an analog of genipin, or a combination thereof; and
   the physical crosslinking agent includes β-glycerophosphate, a derivative of β-glycerophosphate, an analog of β-glycerophosphate, or a combination thereof.

7. The method of Clause 1 wherein the biopolymer includes chitosan, a derivative of chitosan, an analog of chitosan, or a combination thereof.

8. The method of Clause 7 wherein the chemical crosslinking agent includes genipin, a derivative of genipin, an analog of genipin, or a combination thereof.

9. The method of Clause 8 wherein mixing the biopolymer and the chemical crosslinking agent includes mixing the biopolymer and the chemical crosslinking agent such that a weight ratio of the biopolymer to the chemical crosslinking agent is within a range from 10:1 to 100:1.

10. The method of Clause 1, further comprising reinforcing a neck of the aneurysm while the biopolymer and the chemical crosslinking agent are disposed within the internal volume and while the chemical crosslinking is ongoing.

11. The method of Clause 10, further comprising:
intravascularly advancing a balloon toward the portion of the blood vessel while the balloon is in a low-profile state; and
moving the balloon from the low-profile state toward an expanded state after advancing the balloon toward the portion of the blood vessel,
wherein reinforcing the neck includes reinforcing the neck with the balloon in the expanded state.

12. The method of Clause 10, further comprising:
intravascularly advancing a tubular flow diverter toward the portion of the blood vessel while the flow diverter is in a low-profile state; and
moving the flow diverter from the low-profile state toward an expanded state after advancing the flow diverter toward the portion of the blood vessel,
wherein reinforcing the neck includes reinforcing the neck with the flow diverter in the expanded state.

13. A method for treating an aneurysm, the method comprising:
disposing a tissue scaffold material including biopolymer and a chemical crosslinking agent within an internal volume of an aneurysm at a portion of a blood vessel, wherein the tissue scaffold material has a first storage modulus on a pascal scale immediately after being disposed within the internal volume;
reinforcing a neck of the aneurysm while the tissue scaffold material is disposed within the internal volume and while chemical crosslinking of the biopolymer is occurring; and
reducing reinforcement of the neck, wherein the tissue scaffold material has a second storage modulus on a pascal scale immediately after reducing reinforcement of the neck, and wherein the second storage modulus is at least 20% greater than the first storage modulus.

14. The method of Clause 13 wherein the aneurysm is an intracranial aneurysm.

15. The method of Clause 13 wherein:
the chemical crosslinking has an endpoint at which the tissue scaffold material has a third storage modulus on a pascal scale; and
the first storage modulus is within a range from 40% to 80% of the third storage modulus.

16. The method of Clause 13 wherein disposing the tissue scaffold material within the internal volume includes delivering the tissue scaffold material into the internal volume as a single cohesive strand that at least partially agglomerates to form a mass occupying at least 75% of the internal volume, and wherein the internal volume is a total internal volume of the aneurysm.

17. The method of Clause 13 wherein the tissue scaffold material includes a physical crosslinking agent.

18. The method of Clause 17 wherein:
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β-glycerophosphate, a derivative of β-glycerophosphate, an analog of β-glycerophosphate, or a combination thereof.

19. The method of Clause 13 wherein the biopolymer includes chitosan, an analog of chitosan, or a combination thereof.

20. The method of Clause 19 wherein the chemical crosslinking agent includes genipin, a derivative of genipin, an analog of genipin, or a combination thereof.

21. The method of Clause 20 wherein a weight ratio of the biopolymer to the chemical crosslinking agent within the tissue scaffold material is within a range from 10:1 to 100:1.

22. A system for treating an aneurysm, the system comprising:
a first precursor material including a biopolymer;
a second precursor material including a chemical crosslinking agent; and
a catheter including an elongate lumen and an exit port at a distal end portion of the lumen, wherein the catheter is configured to convey a mixture of the first and second precursor materials toward and into an internal volume of an aneurysm at a portion of a blood vessel via the lumen and via the exit port, and wherein the catheter is at most 3 French.

23. The system of Clause 22, wherein the biopolymer has a non-zero degree of chemical crosslinking within the first precursor material.

24. The system of Clause 22 wherein:
(a) the first precursor material includes a physical crosslinking agent;
(b) the second precursor material includes a physical crosslinking agent;
(c) the system further comprises a third precursor material including a physical crosslinking agent; or
(d) any combination of (a), (b) and (c).

25. The system of Clause 24 wherein:
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β-glycerophosphate, a derivative of β-glycerophosphate, an analog of β-glycerophosphate, or a combination thereof.

26. The system of Clause 22 wherein the biopolymer includes chitosan, a derivative of chitosan, an analog of chitosan, or a combination thereof.

27. The system of Clause 26 wherein the chemical crosslinking agent includes genipin, a derivative of genipin, an analog of genipin, or a combination thereof.

28. The system of Clause 22 wherein:
(a) the first precursor material includes a contrast agent;
(b) the second precursor material includes a contrast agent;
(c) the system further comprises a third precursor material including a contrast agent; or
(d) any combination of (a), (b) and (c).

29. The system of Clause 28 wherein the contrast agent is selected to provide diminishing radiopacity.

30. The system of Clause 28 wherein the contrast agent includes iohexol, a derivative of iohexol, an analog of iohexol, or a combination thereof.

31. A method for at least partially filling a volume at a treatment location, the method comprising:
advancing a catheter toward the treatment location, wherein the catheter includes an elongate lumen and an exit port at a distal end portion of the lumen;
mixing a biopolymer and a chemical crosslinking agent to initiate chemical crosslinking of the biopolymer;
flowing the biopolymer and the chemical crosslinking agent toward the volume via the lumen while the chemical crosslinking is ongoing; and delivering the biopolymer and the chemical crosslinking agent from the lumen into the volume via the exit port while the chemical crosslinking is ongoing.

32. The method of Clause 31, wherein advancing the catheter comprises advancing the catheter through a blood vessel.

33. The method of Clause 31, wherein the treatment location comprises an aneurysm and the volume comprises an internal volume of the aneurysm.

34. The method of Clause 31, wherein the treatment location comprises a vein and the volume comprises a lumen of the vein.

35. The method of Clause 34, wherein the vein is located in a leg.

36. The method of Clause 35, further comprising reducing leg vein varicosity by occluding the vein lumen via said delivering.

37. The method of Clause 31, wherein the treatment location comprises an artery that vascularizes a tumor and the volume comprises a lumen of the artery.

38. The method of Clause 31, wherein the treatment location comprises a vascular or cardiovascular implant and the volume comprises an endoleak.

39. The method of Clause 31 wherein:
the biopolymer has a non-zero degree of chemical crosslinking before being mixed with the chemical crosslinking agent; and
mixing the biopolymer and the chemical crosslinking agent includes mixing the biopolymer and the chemical crosslinking agent to increase the degree of chemical crosslinking.

40. The method of Clause 31 wherein delivering the biopolymer and the chemical crosslinking agent from the lumen into the volume includes delivering the biopolymer and the chemical crosslinking agent from the lumen into the volume as components of a single cohesive strand that at least partially agglomerates to form a mass occupying at least 75% of the volume, and wherein the volume is a total internal volume of an aneurysm.

41. The method of Clause 31, further comprising:
flowing a physical crosslinking agent toward the volume via the lumen with the biopolymer and the chemical crosslinking agent; and
delivering the physical crosslinking agent from the lumen into the volume via the exit port with the biopolymer and the chemical crosslinking agent.

42. The method of Clause 41 wherein:
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β-glycerophosphate, a derivative of β-glycerophosphate, an analog of β-glycerophosphate, or a combination thereof.

43. The method of Clause 31 wherein the biopolymer includes chitosan, a derivative of chitosan, an analog of chitosan, or a combination thereof.

44. The method of Clause 43 wherein the chemical crosslinking agent includes genipin, a derivative of genipin, an analog of genipin, or a combination thereof.

45. The method of Clause 44 wherein mixing the biopolymer and the chemical crosslinking agent includes mixing the biopolymer and the chemical crosslinking agent such that a weight ratio of the biopolymer to the chemical crosslinking agent is within a range from 10:1 to 100:1.

46. The method of Clause 31, wherein the treatment location comprises an aneurysm and the volume comprises an internal volume of the aneurysm, and further comprising reinforcing a neck of the aneurysm while the biopolymer and the chemical crosslinking agent are disposed within the internal volume and while the chemical crosslinking is ongoing.

47. The method of Clause 46, further comprising:
intravascularly advancing a balloon toward a portion of a blood vessel near the aneurysm while the balloon is in a low-profile state; and
moving the balloon from the low-profile state toward an expanded state after advancing the balloon toward the portion of the blood vessel,
wherein reinforcing the neck includes reinforcing the neck with the balloon in the expanded state.

48. The method of Clause 47, further comprising:
intravascularly advancing a tubular flow diverter toward the portion of the blood vessel while the flow diverter is in a low-profile state; and
moving the flow diverter from the low-profile state toward an expanded state after advancing the flow diverter toward the portion of the blood vessel,
wherein reinforcing the neck includes reinforcing the neck with the flow diverter in the expanded state.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical, similar, or analogous components or features of more than one embodiment of the present technology.

DETAILED DESCRIPTION

Figure 1:
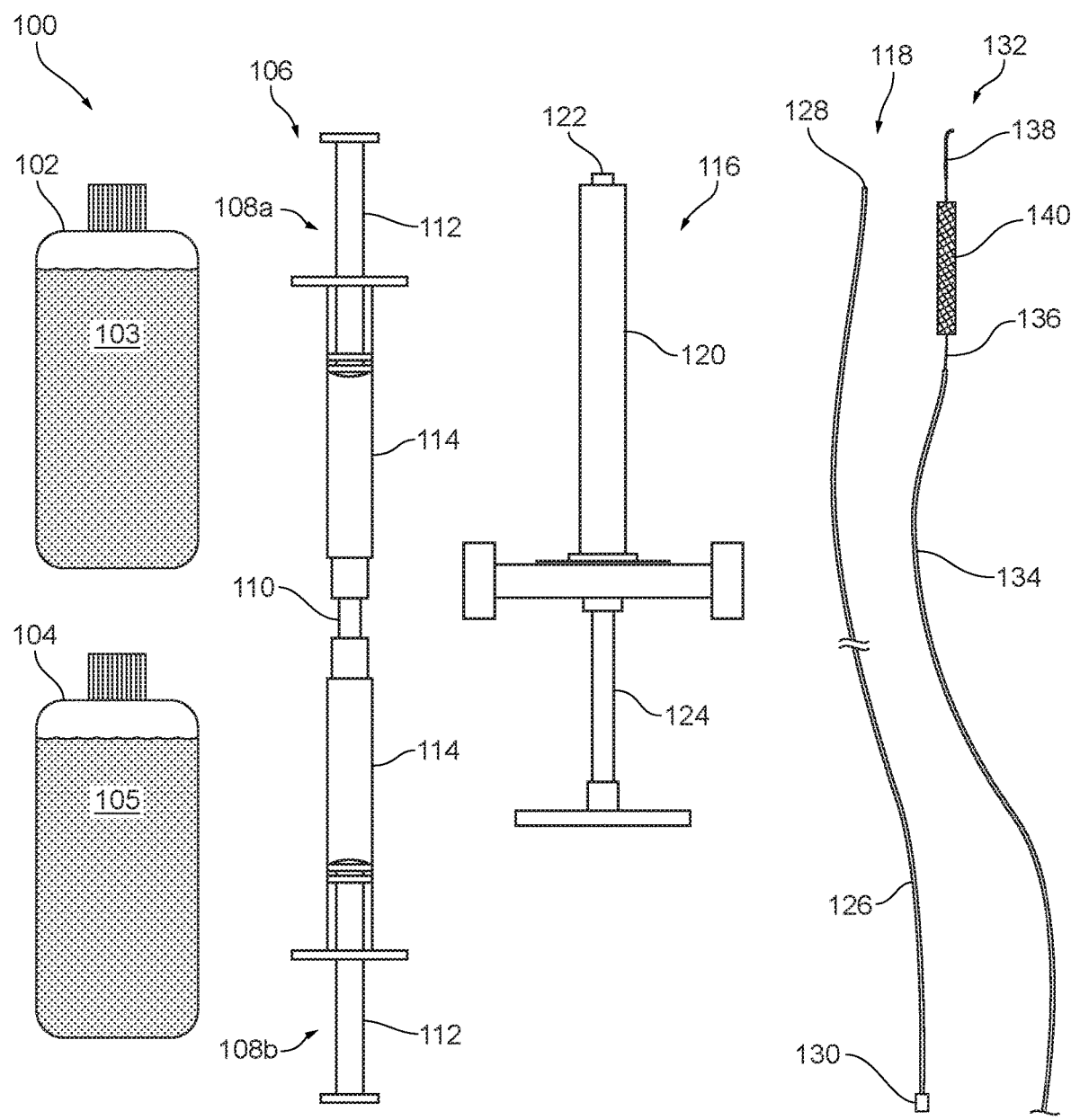
FIG. 1 is a top plan view of a system for treating intracranial aneurysms in accordance with an embodiment of the present technology.

Systems, devices, and methods in accordance with embodiments of the present technology can at least partially address one or more problems associated with conventional technologies whether or not such problems are stated herein. Methods for treating intracranial aneurysms in accordance with at least some embodiments of the present technology include introducing an injectable scaffold material into the internal volume of an intracranial aneurysm (aneurysm internal volume). In animal studies, such methods have been found to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MM imaging and procedures. Embodiments of the present technology can have these and/or other features and advantages relative to conventional counterparts whether or not such features and advantages are described herein.

Specific details of systems, devices, and methods for treating intracranial aneurysms in accordance with embodiments of the present technology are described herein with reference to FIGS. 1-15. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

FIG. 1 is a top plan view of a system 100 for treating intracranial aneurysms in accordance with an embodiment of the present technology. The system 100 can include a first container 102 containing a first precursor material 103 (shown schematically), a second container 104 containing a second precursor material 105 (also shown schematically), and a mixing device 106 suitable for mixing the first and second precursor materials 103, 105. The mixing device 106 can include mixing syringes 108 (individually identified as mixing syringes 108a, 108b) and a coupler 110 extending between respective exit ports (not shown) of the mixing syringes 108. The mixing syringes 108a, 108b each include a plunger 112 and a barrel 114 in which the plunger 112 is slidably received.

The system 100 can further include an injection syringe 116 and a first catheter 118 configured to deliver and receive, respectively, a mixture of the first and second precursor materials 103, 105 from the injection syringe 116. The injection syringe 116 can include a barrel 120, an exit port 122 at one end of the barrel 120, and a plunger 124 slidably received within the barrel 120 via an opposite end of the barrel 120. The first catheter 118 can include an elongate shaft 126 defining an elongate lumen (not shown), an exit port 128 at a distal end portion of the lumen, and a coupler 130 at a proximal end portion of the lumen. The coupler 130 can be configured to form a secure fluidic connection between the lumen and the exit port 122 of the injection syringe 116. The first catheter 118 can be configured to receive a mixture of the first and second precursor materials 103, 105 from the injection syringe 116 via the coupler 130 and to convey the mixture toward and into the internal volume of an intracranial aneurysm (or other treatment location such as any of those described herein) via the lumen and via the exit port 128. The system 100 can further include a second catheter 132 including an elongate sheath 134 and a wire 136 slidably disposed within the sheath 134. At a distal end portion of the wire 136, the second catheter 132 can include an atraumatic hook 138. The first and second catheters 118, 132 can be steerable or non-steerable and can be configured for deployment by guide wire, by guide sheath, or in another suitable manner. Furthermore, the first and second catheters 118, 132 can be of suitable sizes to both be located within an intracranial blood vessel at the same time. In at least some cases, the first catheter 118 is at most 3 French and/or the second catheter 132 is at most 3 French.

The system 100 can also include a tubular stent such as a flow diverter 140 carried by the second catheter 132 proximal to the hook 138. The flow diverter 140 can have an expanded state (as shown) and a low-profile state (e.g., a collapsed state) in which the flow diverter 140 is sufficiently compact to move longitudinally within the sheath 134. In at least some cases, the flow diverter 140 includes filaments that shift relative to one another as the flow diverter 140 moves between its expanded and low-profile states. The flow diverter 140, for example, can be a braided tube.

Figure 2:
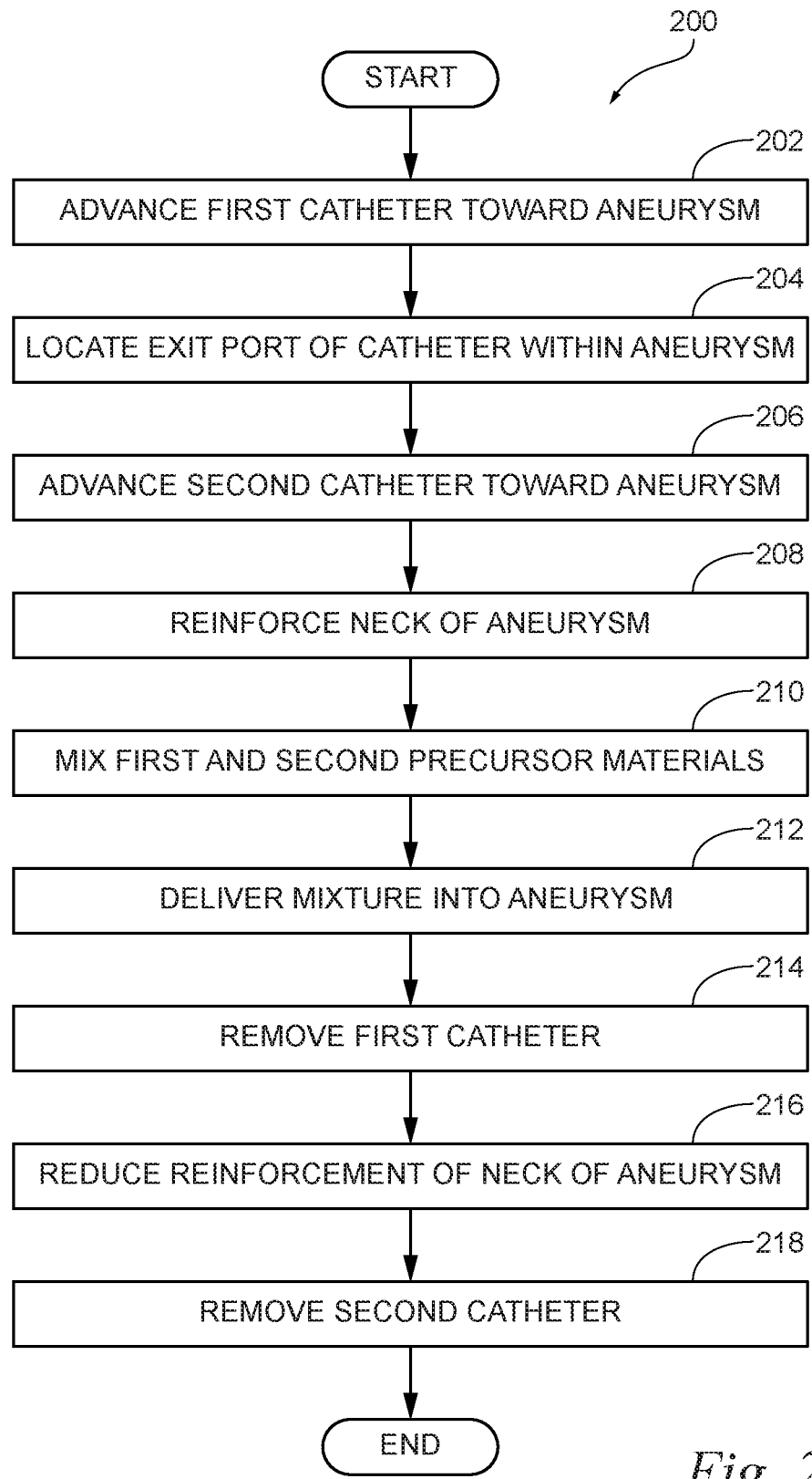
FIG. 2 is a flow chart illustrating a method for treating an intracranial aneurysm in accordance with an embodiment of the present technology.
Figure 3:
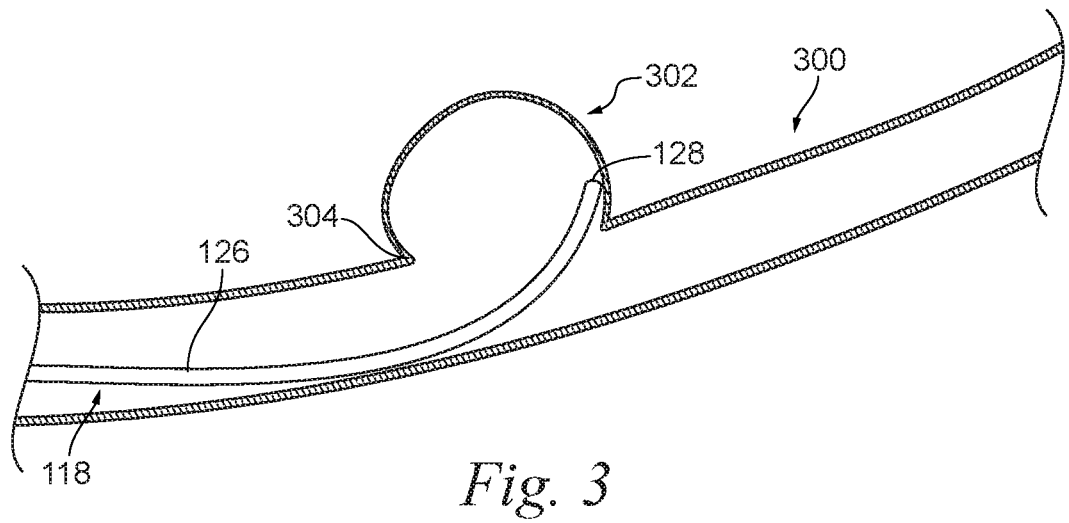
FIGS. 3-12 are anatomical side views of portions of the system shown in FIG. 1 within an intracranial blood vessel at different respective stages during the method shown in FIG. 2.

FIG. 2 is a flow chart illustrating a method 200 for treating an intracranial aneurysm in accordance with an embodiment of the present technology, and FIGS. 3-12 are anatomical side views of portions of the system 100 within an intracranial blood vessel 300 at different respective stages during the method 200. With reference first to FIGS. 2 and 3 together, the method 200 can include intravascularly advancing the first catheter 118 toward an intracranial aneurysm 302 (or other treatment location such as any of those described herein) along the blood vessel 300 (block 202). The method 200 can further include extending the shaft 126 though a neck 304 of the aneurysm 302 to locate the exit port 128 within an internal volume of the aneurysm 302 (block 204). Portions of the first catheter 118 around the exit port 128 can be atraumatic to avoid damaging the aneurysm 302 during positioning of the exit port 128. Although the internal volume of the aneurysm 302 is empty of non-anatomical material or structures in the illustrated embodiment, in other embodiments, the internal volume of the aneurysm 302 may contain such material or structures. For example, the internal volume of the aneurysm 302 may contain a previously introduced embolization coil or mesh. Therefore, the various embodiments of the method 200 can further comprise introduction of a permanent intrasaccular device such as an embolization coil or mesh embolization device (e.g. a mesh coil having a series of expanding petals such as the MEDINA™ Embolization Device from Medtronic). Such embodiments of the method can comprise introducing one or more such permanent intrasaccular devices into the aneurysm before delivering the scaffold material into the aneurysm.

Figure 4:
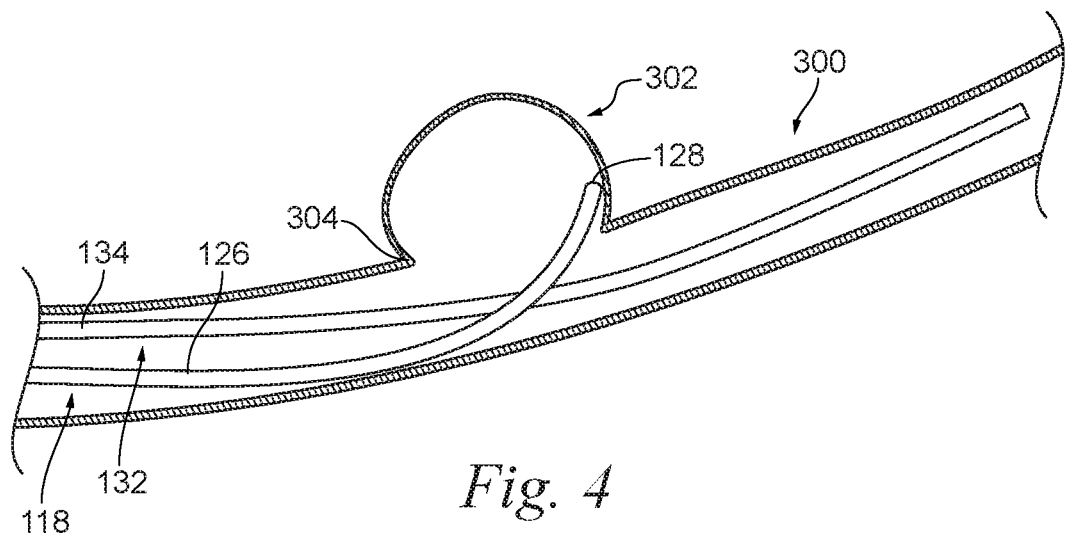
Figure 5:
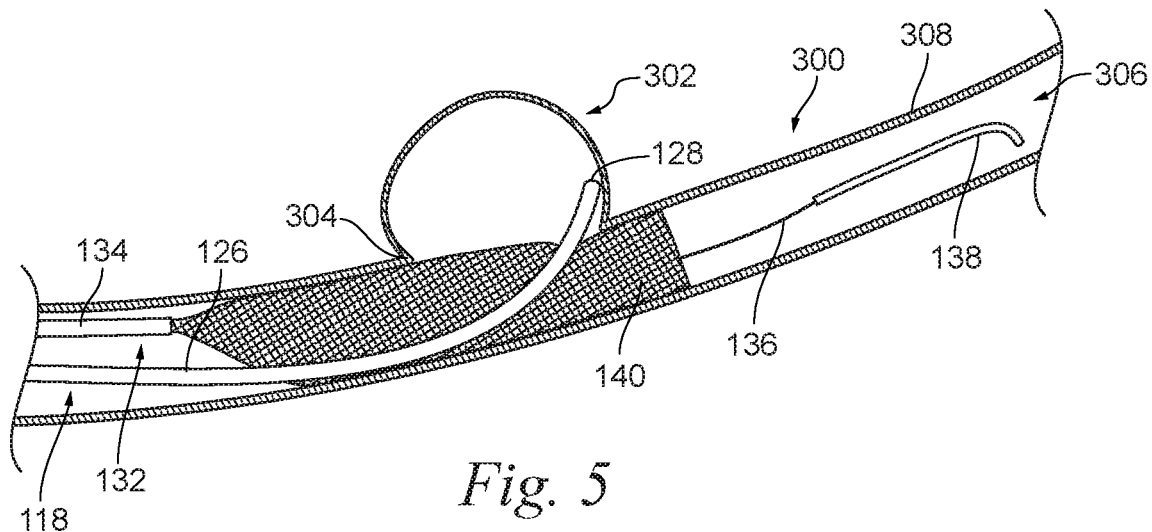

With reference now to FIGS. 1, 2 and 4 together, the method 200 can further include advancing the second catheter 132 toward the aneurysm 302 (block 206) while the flow diverter 140 (FIG. 1) is in its low-profile state. Next, with reference to FIGS. 1, 2 and 5 together, the method 200 can include reinforcing the neck 304 (block 208) by moving the flow diverter 140 from its low-profile state toward its expanded state within a main lumen 306 of the blood vessel 300. In addition to reinforcing the neck 304, the flow diverter 140 can stabilize the position of the exit port 128 within the aneurysm 302 by pressing a portion of the shaft 126 against a wall 308 of the blood vessel 300. In an alternative embodiment, the flow diverter 140 is replaced with a balloon configured to be intravascularly advanced in a low-profile state (e.g., a deflated state) and deployed in an expanded state (e.g., an at least partially inflated state). Use of a balloon in place of a flow diverter may be advantageous, for example, when the intravascular anatomy around an aneurysm is not suitable for deploying a flow diverter. In some cases, a balloon that replaces the flow diverter 140 is a tubular balloon having an annular form or another suitable form with a longitudinal flow passage therethrough for avoiding complete or near complete occlusion of a blood vessel in which the balloon is deployed. Alternatively, a balloon that lacks such a flow passage may be used when such complete or near complete occlusion of a blood vessel is acceptable.

Figure 6:
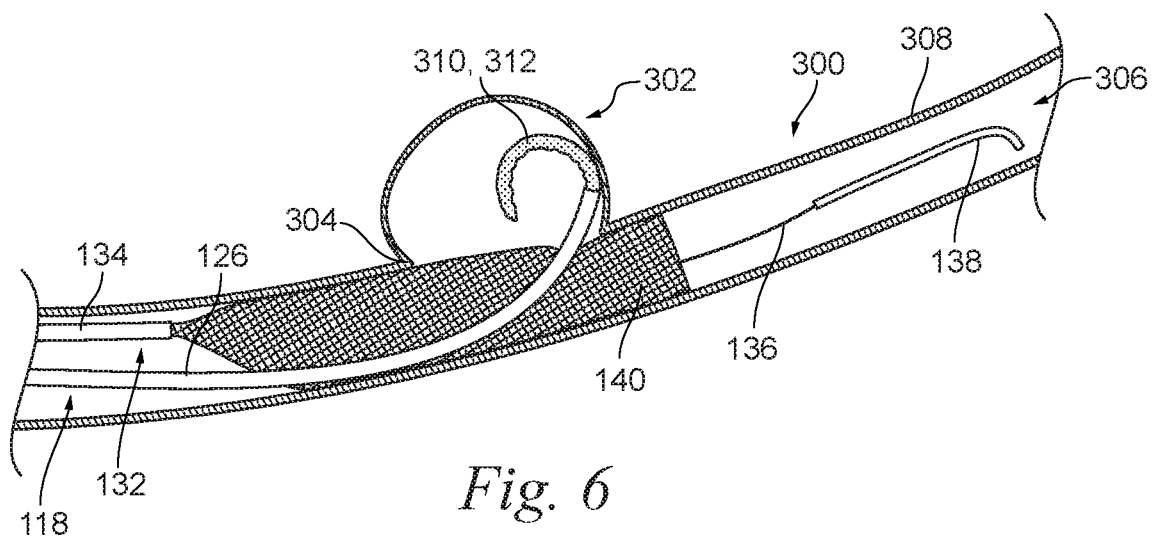

With reference to FIGS. 1, 2 and 6 together, the method 200 can include mixing the first and second precursor materials 103, 105 (block 210) to form a tissue scaffold material 310. In a particular example, the first precursor material 103 is loaded into one of the barrels 114, the second precursor materials 105 is loaded into the other barrel 114, and the mixing syringes 108 are coupled via the coupler 110. To mix the first and second precursor materials 103, 105, the plungers 112 are alternately depressed, thereby causing the first and second precursor materials 103, 105 to move repeatedly from one barrel 114 to the other barrel 114. After suitably mixing the precursor materials, the resulting tissue scaffold material 310 can be loaded into the barrel 120 of the injection syringe 116. When the lumen within the first catheter 118 is very narrow (e.g., when the first catheter 118 is at most 3 French), a considerable amount of pressure may be necessary to move the tissue scaffold material 310 through the lumen to the aneurysm 302. Accordingly, the injection syringe 116 is configured to withstand high pressure, such as at least 500 psi.

The first and second precursor materials 103, 105 (FIG. 1) can include a biopolymer and a chemical crosslinking agent, respectively. The chemical crosslinking agent can be selected to form covalent crosslinks between chains of the biopolymer. In some embodiments, the biopolymer of the first precursor material 103 includes chitosan or a derivative or analog thereof, and the chemical crosslinking agent of the second precursor material 105 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 103 can include collagen or a derivative or analog thereof, and the chemical crosslinking agent of the second precursor material 105 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 103 and the chemical crosslinking agent of the second precursor material 105 can include other suitable compounds alone or in combination.

Mixing the biopolymer of the first precursor material 103 and the chemical crosslinking agent of the second precursor material 105 can initiate chemical crosslinking of the biopolymer. After the first and second precursor materials 103, 105 are mixed, chemical crosslinking of the biopolymer occurs for enough time to allow the resulting tissue scaffold material 310 to be delivered to the aneurysm 302 before becoming too viscous to move through the lumen of the first catheter 118. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the tissue scaffold material 310 to remain within the internal volume of the aneurysm 302 without reinforcing the neck 304.

In at least some cases, the biopolymer has a non-zero degree of chemical crosslinking within the first precursor material 103 before mixing with the chemical crosslinking agent. This can be useful, for example, to customize the curing window for the tissue scaffold material 310 so that it corresponds well with an expected amount of time needed to deliver the material to the aneurysm 302. The degree of chemical crosslinking of the biopolymer within the first precursor material 103 before mixing with the chemical crosslinking agent, the ratio of the biopolymer to the chemical crosslinking agent, and/or one or more other variables can be selected to cause the tissue scaffold material 310 to have a viscosity suitable for delivery to the aneurysm 302 via the lumen of the first catheter 118 for a suitable period of time (e.g., a period within a range from 10 minutes to 40 minutes) after mixing of the first and second precursor materials 103, 105. In at least some cases, the first and second precursor materials 103, 105 are mixed in proportions that cause a weight ratio of the biopolymer to the chemical crosslinking agent in the resulting tissue scaffold material 310 to be within a range from 10:1 to 100:1, such as from 10:1 to 30:1, or from 15:1 to 50:1, or from 15:1 to 25:1. In a particular example, the first and second precursor materials 103, 105 are mixed in proportions that cause a weight ratio of the biopolymer to the chemical crosslinking agent in the resulting tissue scaffold material 310 to be 30:1.

Use of a biopolymer instead of an artificial polymer in the first precursor material 103 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 105 may be advantageous because chemically crosslinked polymers tend to be more cohesive than physically crosslinked polymers and/or for other reasons. In the context of forming a tissue scaffold within an aneurysm, high cohesiveness of the tissue scaffold material 310 may be more important than it is in other contexts to secure the cured tissue scaffold material 310 within the aneurysm 302. For example, high cohesiveness of the tissue scaffold material 310 may reduce or eliminate the possibility of a piece of the tissue scaffold material 310 breaking free and entering a patient's intracerebral blood stream during delivery.

The first and second precursor materials 103, 105 may include other components and/or the system 100 may include other precursor materials intended for mixing with the first and second precursor materials 103, 105. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the tissue scaffold material 310. Suitable physical crosslinking agents for use with chitosan-based biopolymers include glycerophosphate, mannitol, glucose, and derivatives and analogs thereof. In these and other cases, the tissue scaffold material 310 may include multiple chemical crosslinking agents and/or multiple physical crosslinking agents.

A contrast agent is another component that may be added to the precursor materials. The presence of a contrast agent within the tissue scaffold material 310 can be useful to visualize delivery of the tissue scaffold material 310 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the tissue scaffold material 310 is selected to provide radiopacity that diminishes over time. For example, the contrast agent may initially be radiopaque to facilitate delivery of the tissue scaffold material 310 and then become less radiopaque to facilitate follow-up imaging. In a particular example, the first, second, and/or another precursor material includes iohexol or a derivative or analog thereof as a suitable contrast agent.

Figure 7:
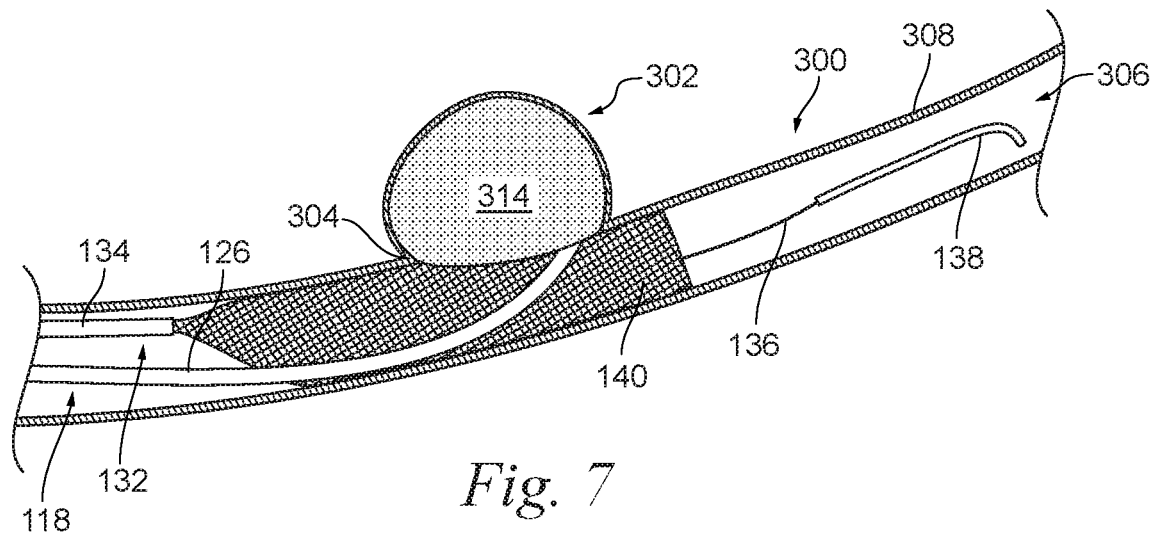

With reference again to FIGS. 1, 2 and 6 together, the method 200 can include delivering the tissue scaffold material 310 into an internal volume of the aneurysm 302 (block 212). For example, the method 200 can include delivering the tissue scaffold material 310 through the lumen of the first catheter 118 so that the tissue scaffold material 310 flows through the exit port 128 of the first catheter 118 and into the aneurysm 302. As the tissue scaffold material 310 passes through the lumen of the first catheter 118, chemical crosslinking of the biopolymer can continue to occur. As shown in FIG. 6, the tissue scaffold material 310 can exit the exit port 128 of the first catheter 118 as a single cohesive strand 312. As shown in FIG. 7, as more tissue scaffold material 310 is delivered to the aneurysm 302, the strand 312 can at least partially agglomerate to form a mass 314. In the illustrated embodiment, the mass 314 occupies all of the internal volume of the aneurysm 302 and the area of the aneurysm neck 304. In other embodiments, the mass 314 can occupy less than all (e.g., from 20% to 100%, from 50% to 100%, or from 75% to 100%) of the total internal volume of the aneurysm 302, particularly but not exclusively when used in combination with additional aneurysm treatments such as embolic coils or implants.

Figure 8:
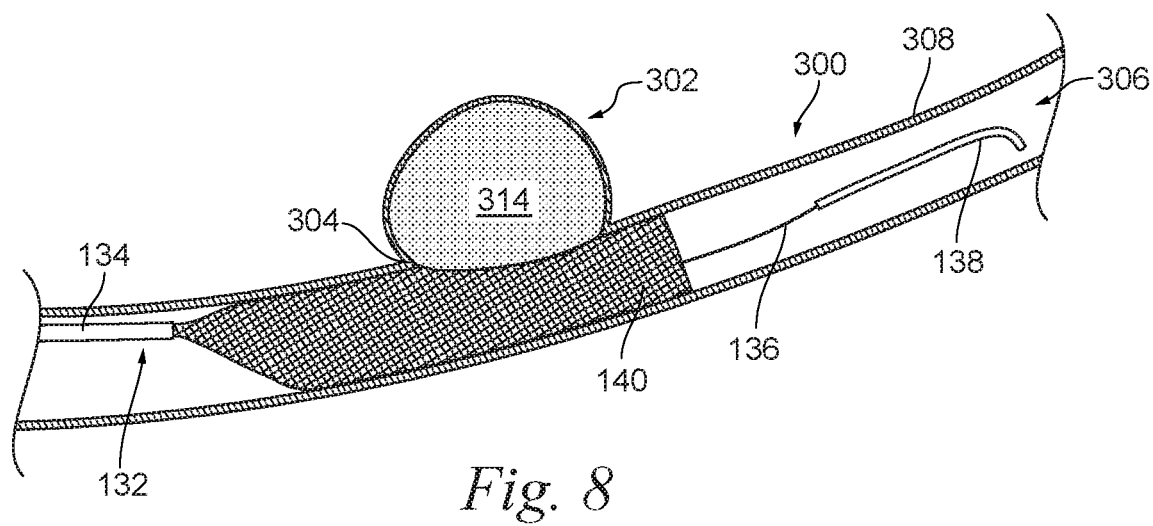

With reference to FIGS. 1, 2 and 8, the method 200 can include removing the first catheter 118 (block 214) after forming the mass 314. The method 200 can further include reinforcing the neck 304 while the tissue scaffold material 310 is disposed within the internal volume of the aneurysm 302 and while chemical crosslinking of the biopolymer continues to occur. The neck 304 can be obstructed by the combination of the mass 314 and the flow diverter 140 (or balloon or other luminal intraluminal device(s)) holding the mass 314 in place until sufficient chemical crosslinking of the biopolymer has occurred.

Figure 9:
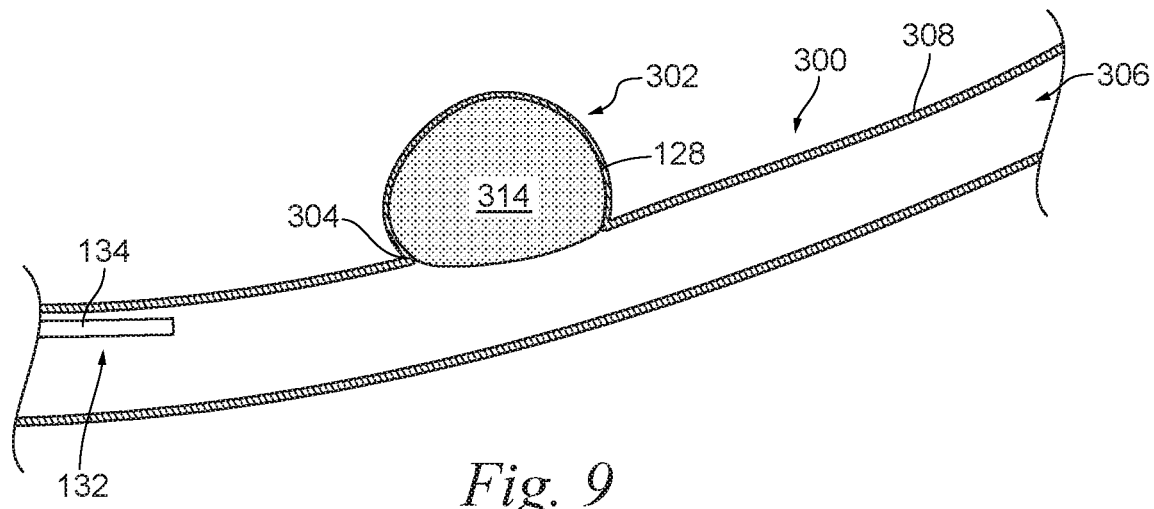

With reference to FIGS. 1, 2 and 9, the method 200 can also include reducing or removing reinforcement of the neck 304 (block 216). For example, the flow diverter 140 can be moved from its expanded state toward its low-profile state and simultaneously or subsequently retracted into the sheath 134. After the tissue scaffold material 310 is disposed within the internal volume of the aneurysm 302 and before the reinforcement of the neck 304 is reduced or removed, the number of chemical crosslinks within the tissue scaffold material 310 may increase by at least 5%, at least 10%, or at least 15%. In at least some cases, the tissue scaffold material 310 has a first storage modulus on a pascal scale immediately after being disposed within the internal volume of the aneurysm 302, a second storage modulus on a pascal scale immediately after reinforcement of the neck 304 is reduced, and a third storage modulus on a pascal scale at an endpoint of the chemical crosslinking. The second storage modulus can be at least 20% greater than the first storage modulus. Furthermore, the first storage modulus can be within a range from 40% to 80% of the third storage modulus.

Figure 10:
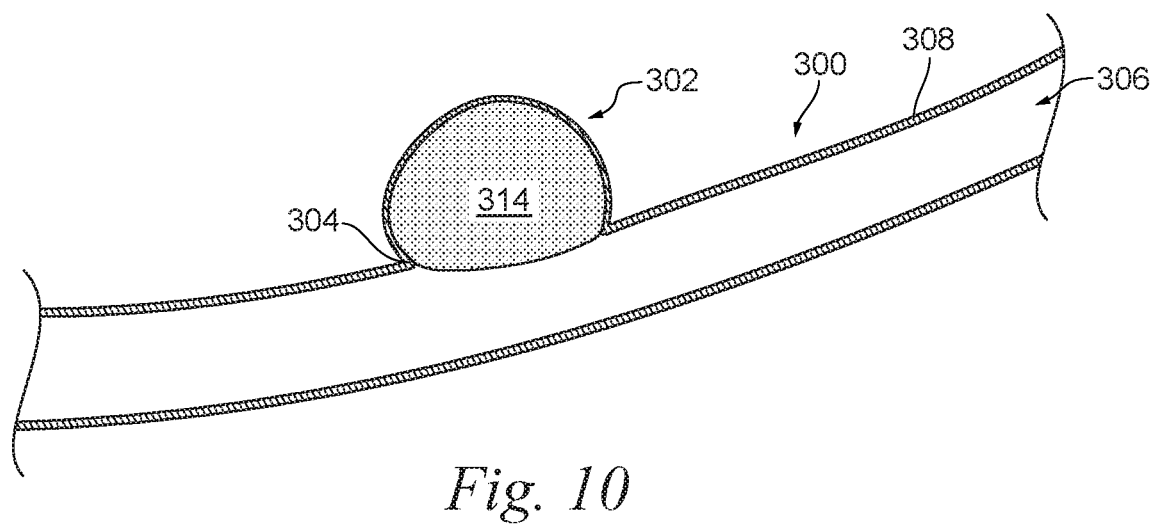
Figure 11:
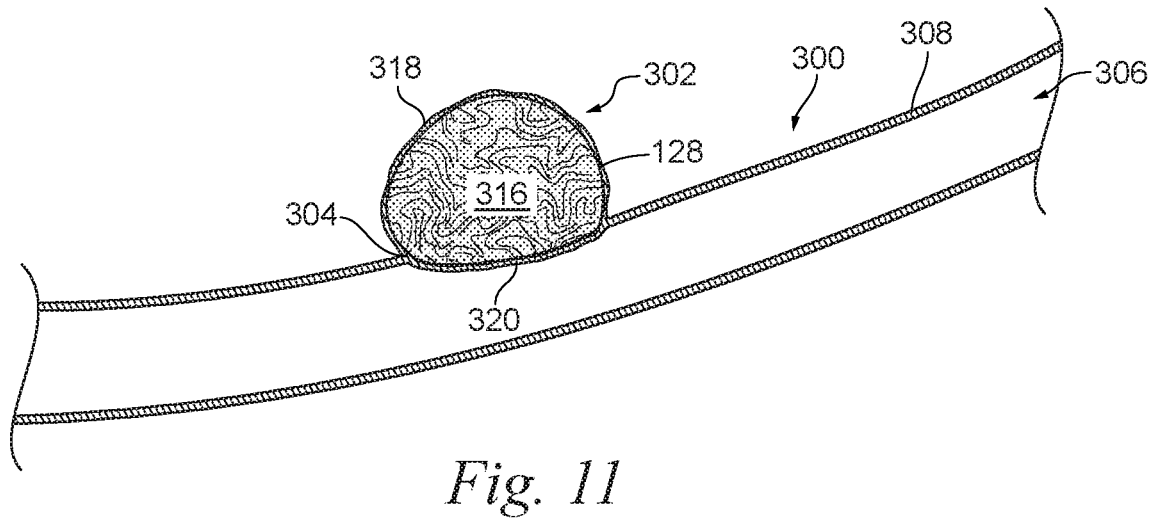
Figure 12:
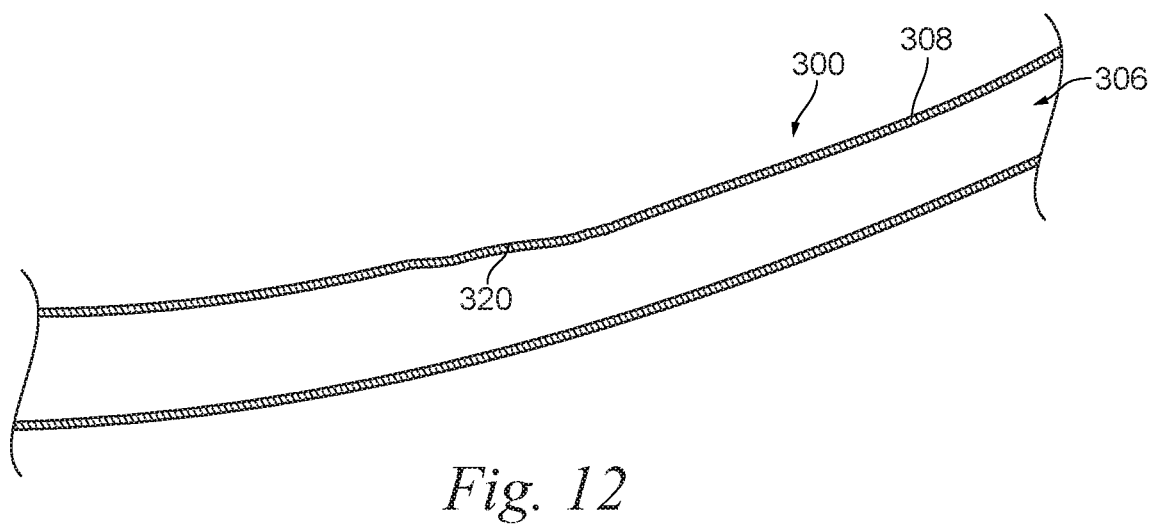

After the flow diverter 140 has been stowed within the sheath 134, the method 200 can include removing the second catheter 132 (block 218). As shown in FIG. 10, the mass 314 can remain securely lodged within the internal volume of the aneurysm 302 after the second catheter 132 is removed. Over time, as shown in FIG. 11, natural vascular remodeling mechanisms and/or bioabsorption of the mass 314 may lead to formation of a thrombus 316 and/or conversion of entrapped thrombus 316 to fibrous tissue within the internal volume of the aneurysm 302. These mechanisms also may lead to cell death at a wall 318 of the aneurysm 302 and growth of new endothelial cells 320 along a surface of the thrombus 316 bordering the main lumen 306 of the blood vessel 300. Eventually, the thrombus 316 and the cells at the wall 318 of the aneurysm 302 may fully degrade, leaving behind a successfully remodeled region of the blood vessel 300 (FIG. 12). In should be noted that, although the flow diverter 140 is removed in the illustrated embodiment, in other embodiment, the flow diverter 140 can be left in place. In these embodiments, the new endothelial cells 320 can grow between and over filaments or struts of the flow diverter 140.

EXAMPLES

The following examples are provided to illustrate certain particular embodiments of the disclosure. It should be understood that additional embodiments not limited to the particular features described are consistent with the following examples.

Example 1—Tissue Scaffold Material

Figure 13:
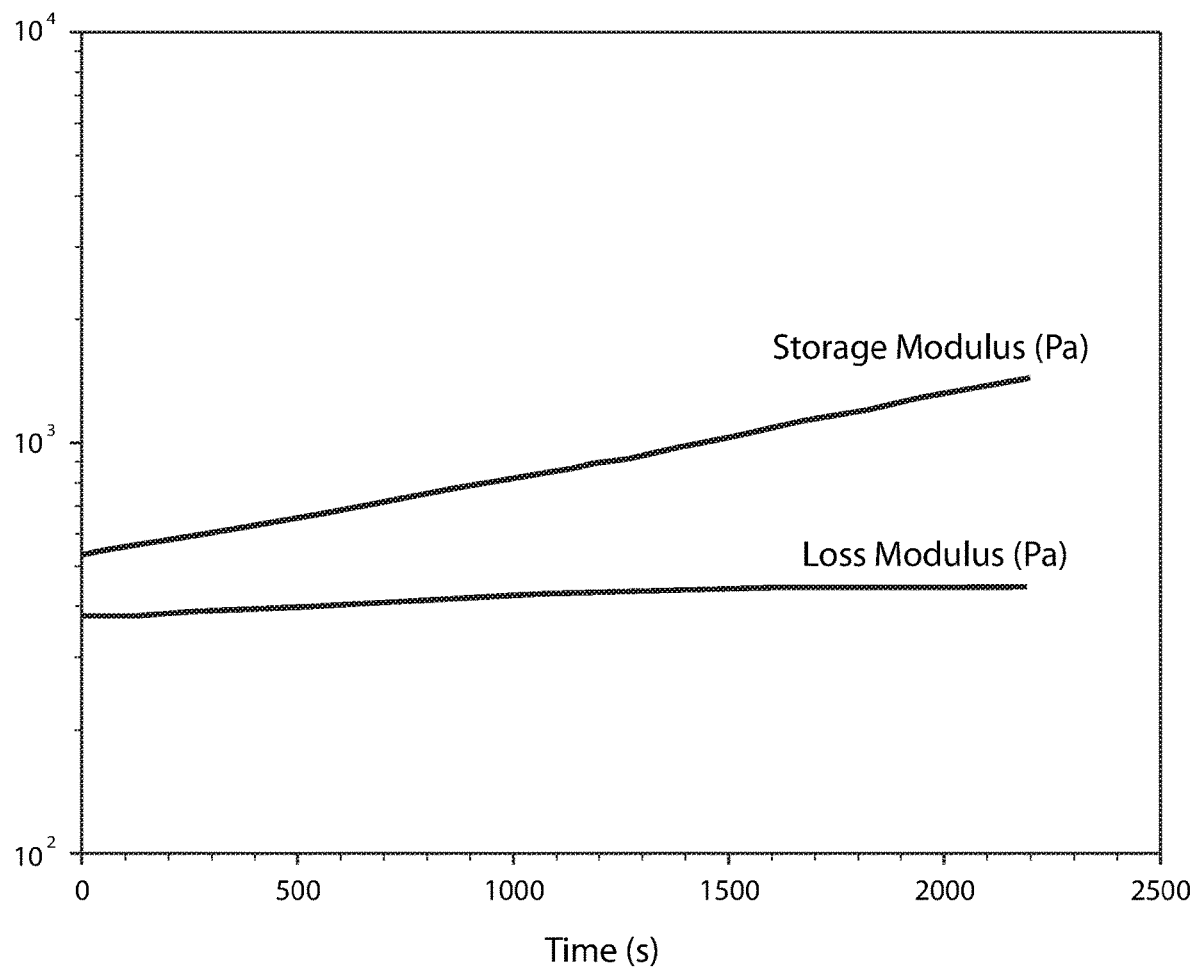
FIG. 13 is a plot of storage modulus (measured by rheometer) and loss modulus (also measured by rheometer) relative to time for a tissue scaffold material in accordance with an embodiment of the present technology.
Figure 14:
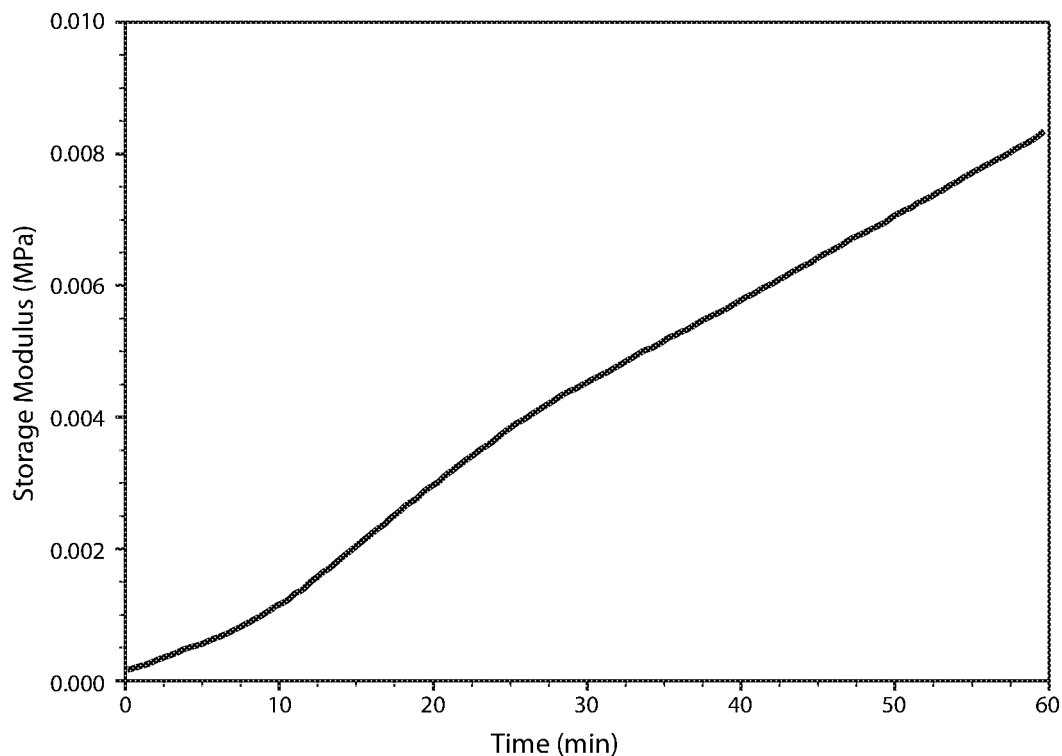
FIGS. 14 and 15 are plots, respectively, of storage modulus (measured by dynamic mechanical analysis) and loss modulus (also measured by dynamic mechanical analysis) relative to time for the tissue scaffold material of FIG. 13.
Figure 15:
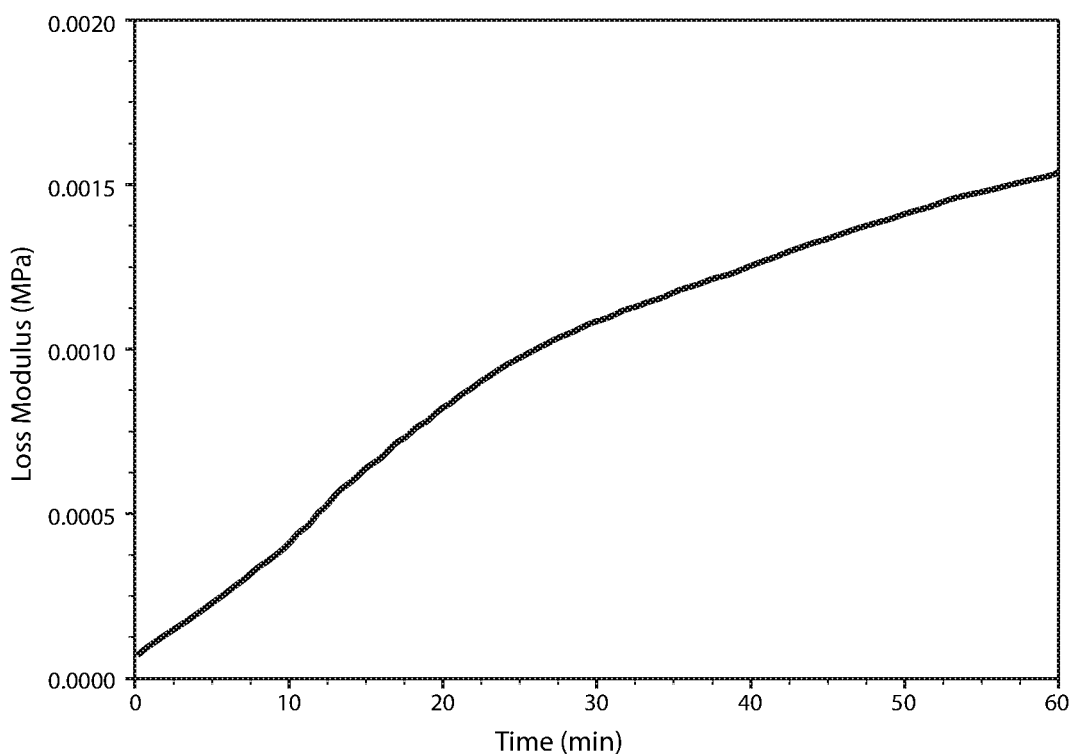

A tissue scaffold material was prepared as a solution of 3.8% chitosan, 2.9% glycerophosphate, and 0.1% genipin (all percentages weight/volume). The ratio of genipin to chitosan in the resulting tissue scaffold material was 38:1. FIG. 13 is a plot of storage modulus and loss modulus relative to time for the tissue scaffold material. The values in FIG. 13 were measured by rheometer beginning 2 minutes after mixing the solutions. Similarly, FIGS. 14 and 15 are plots, respectively, of storage modulus and loss modulus relative to time for the tissue scaffold material. The values in FIGS. 14 and 15 were measured by dynamic mechanical analysis beginning 30 minutes after mixing the solutions. Tissue scaffold materials in accordance with some embodiments of the present technology have storage modulus and/or loss modulus values at a given time after mixing within 25% (e.g., within 10%) of the corresponding values shown in FIGS. 13-15. Tissue scaffold materials in accordance with other embodiments of the present technology can have other suitable storage modulus and loss modulus values.

Example 2—Bench Test

A flow loop with a model aneurysm (10 mm pouch diameter; 4 mm neck diameter) was used for bench testing the tissue scaffold material (Example 1). The distal end of a MARKSMAN® (ID 0.027") microcatheter was located within the model aneurysm and secured by deploying a PIPELINE FLEX™ Embolization Device (Medtronic) ("P-Flex device") across the neck of the model aneurysm. The tissue scaffold material was injected into the model aneurysm via the microcatheter within 10 minutes of mixing the chitosan, glycerophosphate, and genipin solutions. The resulting mass of tissue scaffold material was found to be stable within the model aneurysm for 2 hours under simulated pulsatile blood flow of 600 mL per minute.

Example 3—Animal Test (9-Day Follow Up)

Two model aneurysms (distal and proximal) were created in the carotid artery of each of two canine subjects. The model aneurysms had pouch diameters of approximately 10 mm and neck diameters of approximately 4 mm. Tissue scaffold material (Example 1) was injected into the distal and proximal model aneurysms of the first subject and into the distal model aneurysm of the second subject via the microcatheter (Example 2). P-Flex devices were deployed across the neck of the proximal model aneurysm of the first subject and across the necks of the distal and proximal model aneurysms of the second subject. After 9 days, the subject animals were euthanized and the model aneurysms were biopsied. The biopsies showed that the model aneurysms having the tissue scaffold material and a P-Flex device contained well-developed aneurismal thrombi encompassing all or nearly all of the model aneurysms' internal volumes. The model aneurysm having the tissue scaffold material and not having a P-Flex device included an aneurismal thrombus encompassing most of the model aneurysm's internal volume, but with some vacant areas at the perimeter of the internal volume near the model aneurysm's neck. The model aneurysm having a P-Flex device and not having the tissue scaffold material did not contain an aneurismal thrombus. No inflammation was observed in the parent vessels.

Example 4—Animal Test (90-Day Follow Up)

Two model aneurysms (distal and proximal) were created in the carotid artery of each of two canine subjects. The model aneurysms had pouch diameters of approximately 10 mm and neck diameters of approximately 4 mm. Tissue scaffold material (Example 1) was injected into the distal model aneurysm of the first subject and into the distal and proximal model aneurysms of the second subject via the microcatheter (Example 2). Platinum coils were introduced into the proximal model aneurysm of the first subject. A P-Flex device and a SOLITAIRE® Stent were deployed, respectively, across the necks of the distal and proximal model aneurysms of the first subject. After 90 days, the subject animals were euthanized and the model aneurysms were biopsied. The biopsies showed that the model aneurysms having the tissue scaffold material and not having a P-Flex device or a SOLITAIRE® stent as well as the model aneurysm having the tissue scaffold material and the P-Flex device showed complete endothelial coverage at the aneurismal neck.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like may be used herein to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments of the present technology.

We claim:

1. A system for treating an aneurysm, the system comprising:
    a first precursor material including a biopolymer, wherein the biopolymer has a non-zero degree of chemical cross-linking within the first precursor material;
    a second precursor material including a chemical cross-linking agent; and
    a catheter including an elongate lumen and an exit port at a distal end portion of the lumen, wherein the catheter is configured to convey a mixture of the first and second precursor materials toward and into an internal volume of an aneurysm at a portion of a blood vessel via the lumen and via the exit port.

2. The system of claim 1 wherein the biopolymer includes chitosan, a derivative of chitosan, an analog of chitosan, or a combination thereof.

3. The system of claim 2 wherein the chemical crosslinking agent includes genipin, a derivative of genipin, an analog of genipin, or a combination thereof.

4. The system of claim 1, wherein the catheter is at most 3 French.

5. The system of claim 1, wherein:
(a) the first precursor material includes a physical crosslinking agent;
(b) the second precursor material includes a physical crosslinking agent;
(c) the system further comprises a third precursor material including a physical crosslinking agent; or
(d) any combination of (a), (b) and (c).

6. The system of claim 1, wherein:
(a) the first precursor material includes a contrast agent;
(b) the second precursor material includes a contrast agent;
(c) the system further comprises a third precursor material including a contrast agent; or
(d) any combination of (a), (b) and (c).

7. The system of claim 1, further comprising:
a physical cross-linking agent comprising β-glycerophosphate, a derivative of β-glycerophosphate, an analog of β-glycerophosphate, or a combination thereof; and
a contrast agent comprising iohexol, a derivative of iohexol, an analog of iohexol, or a combination thereof.

8. The system of claim 7, wherein the biopolymer includes chitosan, a derivative of chitosan, an analog of chitosan, or a combination thereof, and wherein the chemical crosslinking agent includes genipin, a derivative of genipin, an analog of genipin, or a combination thereof.

9. The system of claim 1, wherein a weight ratio of the biopolymer:chemical crosslinking agent is within a range of from 10:1 to 100:1.

10. A system for treating an aneurysm, the system comprising:
a first precursor material including a biopolymer;
a second precursor material including a chemical crosslinking agent; and
a catheter including an elongate lumen and an exit port at a distal end portion of the lumen, wherein the catheter is configured to convey a mixture of the first and second precursor materials toward and into an internal volume of an aneurysm at a portion of a blood vessel via the lumen and via the exit port,
wherein:
(a) the first precursor material includes a physical crosslinking agent;
(b) the second precursor material includes a physical crosslinking agent;
(c) the system further comprises a third precursor material including a physical crosslinking agent; or
(d) any combination of (a), (b) and (c).

11. The system of claim 10 wherein:
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β-glycerophosphate, a derivative of β-glycerophosphate, an analog of β-glycerophosphate, or a combination thereof.

12. The system of claim 10, wherein the biopolymer includes chitosan, a derivative of chitosan, an analog of chitosan, or a combination thereof.

13. The system of claim 10, wherein a weight ratio of the biopolymer:chemical crosslinking agent is within a range of from 10:1 to 100:1.

14. The system of claim 10, wherein the physical crosslinking agent comprising β-glycerophosphate, a derivative of β-glycerophosphate, an analog of β-glycerophosphate, or a combination thereof, the system further comprising:
a contrast agent comprising iohexol, a derivative of iohexol, an analog of iohexol, or a combination thereof.

15. A system for treating an aneurysm, the system comprising:
a first precursor material including a biopolymer;
a second precursor material including a chemical crosslinking agent; and
a catheter including an elongate lumen and an exit port at a distal end portion of the lumen, wherein the catheter is configured to convey a mixture of the first and second precursor materials toward and into an internal volume of an aneurysm at a portion of a blood vessel via the lumen and via the exit port,
wherein:
(a) the first precursor material includes a contrast agent;
(b) the second precursor material includes a contrast agent;
(c) the system further comprises a third precursor material including a contrast agent; or
(d) any combination of (a), (b) and (c).

16. The system of claim 15 wherein the contrast agent is selected to provide diminishing radiopacity.

17. The system of claim 15 wherein the contrast agent includes iohexol, a derivative of iohexol, an analog of iohexol, or a combination thereof.

18. The system of claim 15, wherein the biopolymer includes chitosan, a derivative of chitosan, an analog of chitosan, or a combination thereof.

19. The system of claim 15, wherein a weight ratio of the biopolymer:chemical crosslinking agent is within a range of from 10:1 to 100:1.

20. The system of claim 15, wherein the catheter is at most 3 French.

* * * * *

UNITED STATES PATENT AND TRADEMARK OFFICE
CERTIFICATE OF CORRECTION

PATENT NO. : 10,576,099 B2
APPLICATION NO. : 15/299929
DATED : March 3, 2020
INVENTOR(S) : Junwei Li et al.

It is certified that error appears in the above-identified patent and that said Letters Patent is hereby corrected as shown below:

On the Title Page

Item (72), Column 1, in "Inventors", Line 4, delete "Lyons" and insert -- Lyon --, therefor.

Signed and Sealed this
Seventh Day of April, 2020

Andrei Iancu
*Director of the United States Patent and Trademark Office*